US006051730A

United States Patent [19]
Pallas et al.

[11] Patent Number: 6,051,730
[45] Date of Patent: Apr. 18, 2000

[54] SURFACTANT CLATHRATES AND AGRICULTURAL CHEMICAL FORMULATIONS THEREOF

[75] Inventors: Norman R. Pallas, Freehold; James L. Hazen, Plainsboro, both of N.J.

[73] Assignee: Rhodia Inc., Cranbury, N.J.

[21] Appl. No.: 08/850,455

[22] Filed: May 5, 1997

[51] Int. Cl.$^7$ ...................................................... C07F 7/10
[52] U.S. Cl. .......................... 556/419; 556/423; 556/425; 71/11; 514/63; 504/101; 504/164; 504/193; 424/DIG. 8; 424/DIG. 10
[58] Field of Search .................................... 556/425, 419, 556/423; 71/11; 564/63; 504/101, 164, 193; 424/DIG. 8, DIG. 10

[56] References Cited

U.S. PATENT DOCUMENTS

| | | |
|---|---|---|
| 2,520,716 | 8/1950 | Fetterly . |
| 2,569,984 | 10/1951 | Fetterly . |
| 3,299,112 | 1/1967 | Bailey et al. . |
| 3,562,786 | 2/1971 | Bailey et al. . |
| 4,933,002 | 6/1990 | Petroff et al. . |
| 5,017,216 | 5/1991 | Petroff et al. . |
| 5,059,704 | 10/1991 | Petroff et al. . |
| 5,087,715 | 2/1992 | Snow ....................................... 556/413 |
| 5,104,647 | 4/1992 | Policello . |
| 5,145,978 | 9/1992 | Petroff et al. . |
| 5,482,529 | 1/1996 | Ahlnas et al. ........................... 504/101 |
| 5,583,089 | 12/1996 | Winston .................................. 504/101 |
| 5,627,251 | 5/1997 | Sato et al. ................................. 528/15 |
| 5,739,369 | 4/1998 | Matsumura et al. ..................... 556/425 |

FOREIGN PATENT DOCUMENTS

| | | |
|---|---|---|
| 2093377 | 4/1993 | Canada . |
| 242592 | 4/1969 | U.S.S.R. . |
| WO89/12394 | 12/1989 | WIPO . |
| WO94/22311 | 10/1994 | WIPO . |

OTHER PUBLICATIONS

J. Radell and P. D. Hunt, "Occlusion of Organosilanes by Urea", *Journal American Chemical Society*, vol. 80, pp. 2683–2685 (1958).

R. Davis, "Solid Adjuvants Based on Urea–Surfactant Adducts", A Presentation on Behalf of I.C.I. Americas, Inc., Wilmington, DE. (1993).

F. E. Bailey, Jr., and H. G. France, "Molecular Association Complexes of Polymers. Urea and Thiourea Complex of High Molecular Weight Poly(Ethylene Oxide)", *Journal of Polymer Science*, vol. 49, pp. 397–406 (1961).

L. Mandelcorn, "Clathrates", *Chemical Reviews*, vol. 59, pp. 827–839 (1959).

L. C. Fatterly, "Study of Kinetic and Equilibria of Urea–Fatty Acid and Related Complexes", PhD. Thesis, Univ. of Washington, Seattle (1950).

E. Makin, "Clathration", *Encyclopedia of Chemical Technology*, vol. 6, pp. 179–189 (John Wiley & Sons, New York, N. Y.).

V. D. Simonov, et al., "Use of Clathrate Compounds of Urea with Surfactants in the Production of Pesticidal Preparations",*Dokl. Neftekhim. Sekts. Bashkir. Respub. Pravl. Vses. Khim. Obshchest.* 6:326–9, 15 (1971) from: Ref.. Zh., Khim. 1972, Abstr. No. 4N648. [Translation Enclosed].

L. Jansen, "Enhancement of Herbicides by Silicone Surfactants", *Weed Science*, vol. 21, Issue No. 2, pp. 130–135 (Mar. 1973).

B. Hardman and A. Torkelson, "Silicones", *Encyclopedia of Polymer Science and Engineering*, vol. 15, pp. 204–308 (John Wiley & Sons, New York, N. Y., 1989).

"Silicones for the Agricultural Industry", Union Carbide Technical Brochure, pp. 1–24.

H. M. Powell, "Clathrates", *Non–Stoichiometric Compounds*, Chapter 7, pp. 439–489, (Academic Press, Inc., New York, N.Y.,1964).

L. C. Fetterly, "Organic Adducts", *Non–Stoichiometric Compounds*, Chapter 8, pp. 491–567, (Academic Press, Inc., New York, N.Y.,1964).

L. A. K. Staveley, "Physics and Chemistry of Inclusion Complexes", *Non–Stoichiometric Compounds*, Chapter 10, pp. 607–635, (Academic Press, Inc., New York, N.Y., 1964).

*Primary Examiner*—Paul F. Shaver
*Attorney, Agent, or Firm*—John Daniel Wood

[57] ABSTRACT

A solid, water-soluble complex comprising:

a) a water-miscible polysiloxane of the formula:

$$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_y\left[\underset{\underset{\underset{O-(C_2H_4O)_a(C_3H_6O)_bR}{|}}{C_nH_{2n}}}{\overset{\overset{CH_3}{|}}{Si}}-O\right]_x\underset{\underset{CH_3}{|}}{\overset{\overset{CH_3}{|}}{Si}}-CH_3$$

wherein n is from 2 to 6; a is from 8 to 25; and b is from 0 to 25; and the oxyalkylene groups may be random or block mixtures; y is from 0 to 5; x is from 1 to 5; and R is selected from the group consisting of hydrogen, $C_1$–$C_4$ alkyl, and a $C_1$–$C_4$, alkyl ester; or $$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_y\left[\underset{\underset{A}{|}}{\overset{\overset{CH_3}{|}}{Si}}-O\right]\left[\underset{\underset{G}{|}}{\overset{\overset{CH_3}{|}}{Si}}-O\right]_x\underset{\underset{CH_3}{|}}{\overset{\overset{CH_3}{|}}{Si}}-C$$

wherein A is a linear or branched alkyl having 6 to 30 carbon atoms; G is a glycol moiety of the formula —R' $(OCH_2CH_2)_m$ OR" wherein R' is a divalent alkylene group having 2 to 6 carbon atoms; R" is selected from the group consisting of hydrogen, $C_1$–$C_4$ alkyl, and a $C_1$–$C_4$ alkyl ester; m is 8 to 100; y is 0 to 5; X is 0.1 to 2.5; and z is 0.1 to 5.0; and b) a complex-forming agent of the formula:

$$H_2N-\overset{\overset{X}{\|}}{C}-NH_2$$

wherein X is O, S, Sc, or Te.

These complexes are useful useful as adjuvants for dry agricultural chemicals such as pesticides and/or fertilizers.

20 Claims, 3 Drawing Sheets

SURFACTANT CLATHRATES AND AGRICULTURAL CHEMICAL FORMULATIONS THEREOF

FIELD OF THE INVENTION

This invention relates to dry silicone products specifically complexes of urea with ethoxylated silicones and methods for preparing same. These solid, free-flowing water-soluble complexes are especially useful as adjuvants for dry agricultural chemicals such as pesticides and/or fertilizers.

BACKGROUND OF THE INVENTION

Silicone surfactants, or more properly, organosilicones exhibit unusual properties that account for their use in a large number of specialty applications. For example, many have excellent wetting and penetrating characteristics.

The term silicone denotes a synthetic polymer which contains a repeating silicon-oxygen backbone and has organic groups attached to a significant proportion of the silicon atoms by silicon-carbon bonds. In commercial silicones, most R groups are methyl, higher alkyl, fluoralkyl, phenyl, vinyl, and a few other groups substituted for specific purposes; e.g., hydrogen, chlorine, alkoxy, acyloxy, and alkylamino.

Commercially useful silicone products are usually made by the process whereby silica is catalytically reacted with an RCR group which is usually methyl chloride. Hydrolysis of the organochlorosilanes formed yield the siloxane structures which are the bases of many silicon products as outlined in the reaction scheme I $$2R_2SiCl2 + 4H_2O \longrightarrow 2[R_2Si(OH)_2] + 4HCl$$

(Unstable)

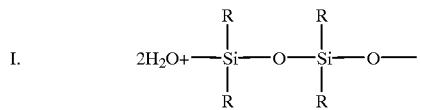

I.

The three commercially important classes of silicone polymers include silicone homopolymers, silicon random copolymers, and silicone-organic (block) copolymers. Polydimethylsiloxanes (II) constitute by far the largest volume of homopolymers produced today.

II.

Polydimethylsiloxane is usually the principal component of the random copolymers and the principal siloxane building block or component of most silicone-organic copolymers.

The molecular weight of the polysiloxanes is usually controlled by the chain terminating groups. The trimethylsiloxy group from hexamethyl disiloxane (III) results in polymers that do not polymerize further by chain extension.

III. 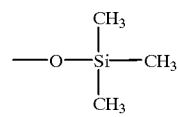

In fact, the first known silicones are the trimethylsiloxy-terminated siloxanes. The properties of these siloxanes are modified by substitution of the methyl groups on the silicon atom in the —Si—O—backbone by hydrogen, alkyl, phenyl, or organofunctional groups.

Structurally, organosilicones derive their a polar (hydrophobic) properties from the siliconbased rather than carbon-based moieties. Polar groups, such as ethylene oxide chains, can be introduced into copolymers to provide enhanced hydrophilic properties. Common silicone surfactants are derivatives of monomethyl and dimethyl silicone compounds which are conjugated with ethylene or propylene oxide chains (glycols) or with substituted aliphatic carbon moieties containing amino or carboxyl substituents.

As a result of the weak intermolecular forces and the very high flexibility and rotational freedom that exist on the backbone of these polymers, linear siloxanes have very low melting points, do not crystallize under ordinary conditions; and, in fact, many are liquid at room temperatures.

As mentioned above, silicones have an unusual array of properties. Chief among these are thermal and oxidating stability and physical properties little affected by temperature. Other salient properties include resistance to weathering, ozone, and radiation; low surface tension; high surface activity; good spreading power; and, when unmodified, chemical and biological inertness.

Nonionic surfactants are commonly used as agricultural adjuvants to improve the efficacy of pesticides such as herbicides, fingicides, growth regulators, biologicals, and micronutrients. The surfactants play several roles in these agricultural formulations. For example, as activator agents, they can enhance the biological effectiveness of a pesticide. As a compatibility agent, they can selectively reduce or eliminate undesirable chemical interactions of two or more agrichernicals in a formulation and/or improve homogeneity of, for example, fertilizer with other agrichemicals in the mixture. As wetting or spreading agents, via reduction of surface tension in aqueous solutions, they increase the surface area covered by a given volume of the agricultural formulation. This is especially important for the spreading of solutions on difficult to wet surfaces such as a waxy leaf cuticle. The nonionic surfactants also aid in the uptake of active ingredients into plant tissue through permeation of the cuticle, through defects in the surface, and in some special cases, through flooding of the leaf stomata. Urea, ammonium nitrate, diammonium phosphate, and diammonium sulfate are also often used as agricultural adjuvants to supply nitrogen to crops and often, serendipitously to enhance the biological efficacy of pesticide formulations.

Certain organosilicone compounds have been recognized as excellent agricultural adjuvants, because of their outstanding wetting characteristics, enhancement of foliar uptake, and unique ability to increase the overall bioefficacy of many pesticide formulations especially those formulations containing glyphosate as the primary active.

Most of the organosilicone adjuvants, however, have the distinct disadvantage of being liquids, pastes or soft waxes at ambient temperatures. Thus, they are extremely difficult to include uniformly in dry pesticidal formulations. Attempts to overcome this liquid problem have utilized various adsorbents such as clays or silicas as solid carriers. However, these solid carriers are not soluble in water, not biologically active, clog fine spray lines and nozzles, and increase nozzle wear. Often, the surfactants are heated prior to blending to ease handling by decreasing viscosity which may, in turn, have a negative effect on its or the blend components chemical stability. In addition to the difficulties encountered in attempting to obtain uniform distribution of liquid surfactant in a powdered or particulate blend, the resulting tackiness ofttimes results in masses of material sticking to the walls of the blending apparatus.

In view of the above, it would be highly desirable to be able to produce agriculturally useful, oganofunctional polysiloxanes in a dry state.

Clathrates, also referred to as inclusion complexes are single-phased solids consisting of two distinct components; with the molecule of one component being retained in closed cavities or cages provided by the crystalline structure of the molecules of the second component. The two components of a clathrate do not react chemically with each other, but the solid clathrates have sharp melting points and always show integral values for the molecular ratios of the two components.

In contrast, a more recently explored class of inclusion complexes also known as tube, channel or canal inclusion complexes or adducts, form needle crystals and exhibit a lack of conformity to the classical law of simple multiple proportions. The most widely known examples of these non-stoichiometric complexes are the channel adducts of urea-n-paraffin, and thioureabranched chain paraffins. The molecules of one component are bound together, usually by hydrogen bonds, to give rise to large tubular intertwining polymer networks in which the molecules of the second component may become entrapped, anchored, or stabilized. The compound which traps or encloses another molecule has become known as the host, and molecules which become enclosed are often called the guest molecules. Two unique properties of these channel inclusion complexes are that they do not exist in solution in exactly the same form as they do in the crystalline state and their constituents do not exist in the crystalline aggregates in ratios of exact whole numbers. Since the urea and thiourea complexes have a non-stoichiometric ratio between the guest and host molecules which are governed by crystalline dimensions, it is impossible for them to exist in solution in exactly the same form as they exist in the crystalline, solid state. They form only as continuous crystalline host lattices and, although they sometimes appear to lack conventional bonding, many of these complexes are quite stable. The host molecules molecularly encapsulate and thereby modify the apparent physical and chemical properties of the guest molecules. An unusual property of the organic channel adducts is that their stability depends in part upon a very exact fit within the tubular cavity or cavities which the host molecules can form; thus we are also dealing with substances which depend on the size and shape of the guest molecules for interaction.

Early work with n-paraffms found that urea and thioureas form the channel molecular inclusion complexes, that is, the urea and thiourea molecules form a hollow channel just large enough to accommodate the planar zigzag of the n-paraffm hydrocarbon molecule; essentially large interpenetrating helical spirals forming a nearly circular dimensioned, or hexagonal latticed channel with the hydrocarbon molecules at the center.

Urea by itself forms a tetragonal structure, however, a crystalline transformation to the hexagonal structure occurs when an inclusion complex is formed.

Among the straight chained hydrocarbons, n-hexane is the smallest member which has formed an inclusion complex with urea. In general, with any homologous series, the stability of the inclusion complexes, i.e., the ability to form a separable, dry precipitate, increases with the chain length of the guest molecule. Large end groups have a negative effect on the formation of channel complexes which often can be overcome by significantly increasing the length of the hydrocarbon chain being complexed.

A number of other n-aliphatic organic compounds, besides the straight paraffinic chains have been reacted with urea. Fatty acid series have been studied as well as inclusion complexes of the n-alcohols, esters, halides, diglycerides, dibasic acids, olefins, and many related normal aliphatic structures. Inclusion complex studies of homologous series involving maleate, fumarate, and fluorinated esters have been reported.

With each class of compounds or homologous series, there is a minimum chain length which is required for adduct formation. For n-paraffins, the minimum chain length is six carbons at room temperature and pressure, but under pressure and at lower temperatures, even propane can be made to react. There is no theoretical upper limit to the length of paraffim chains which will complex with urea. In fact, urea channel adducts have been formed by reaction with poly (ethylene oxide) polymers as high as 4,000,000 in molecular weight.

Clathrates are generally prepared by recrystallization and precipitation from solution. If the host is soluble in the guest component, the preparation is simple. Otherwise, it is necessary to use a common solvent which cannot be clathrated by the host. Water is typically the solvent of choice. Of course, in crystallizing solutions where the concentration of the guest component is low, stirring and slow crystallization are necessary to avoid depletion of the guest component at the site of crystallization after initial clathrate formation.

Radell and Hunt (J. Am. Chem. Soc. 80, 2683 (1958)) prepared urea inclusion complexes of three monoalkylsilanes and four dialkylsilanes and reported that the complexes were white crystalline solids with "the melting point of urea". They noted that although hexane is the shortest hydrocarbon molecule that will form a crystalline urea complex under normal conditions, neither amylsilane nor hexylsilane would form such a crystalline structure. Thus they concluded that although a single silicon atom per se in the backbone of a linear hydrocarbon chain does not prevent the formation of a urea inclusion complex, it has a destabilizing influence.

In 1993, R. Davis of ICI Surfactants presented a paper entitled Solid Adjuvants Based On Urea-Surfactant Adducts in which he proposed that certain agrochemical surfactants would be good candidates for urca complexation, i.c., for conversion into free flowing powders. Among those suggested were, polyethylene glycols; EO/PO block copolymers; and ethoxylated alcohols, acids, and nonyl phenols. Ethoxylated tridecyl alcohol was exemplified. Davis also proposed that once such urea-surfactant adducts were formed, other adjuvants could be added to change the adjuvant properties of the final product such as phosphate ester acidifying agents, ethoxylated silicone wetting agents, and various sticking agents.

L. C. Fetterly (Study of Kinetics and Equilibria of Urea-Fatty Acid and Related Complexes, Ph.D. Thesis, University of Washington, Seattle, 1950) suggested that linear silicon polymers probably do not form inclusion complexes because the chain diameter is too large. He, in fact, tried to prepare complexes of these polymers, as well as an inclusion complex of dichlorosilane from urea and thiourea and was unable to do so. Illustrative of the sensitivity of the inclusion complexes to the diameter of the guest molecule, Fetterly noted that whereas normally one can form a urea inclusion complex with an n-paraffin carbon chain of 6 or greater; a linear paraffin chain of almost 18 C-atoms in length is required to off-set the distortion caused by a single methyl group in the 2 position.

Since it is presently impossible in most instances to predict solid molecular crystalline structure a priori, the discovery of a new clathrate or clathratable material has been and still is a matter of chance.

OBJECT OF THE INVENTION

It is an object of this invention to prepare solid, free-flowing adjuvants from initially liquid ethoxylated polysiloxanes.

It is also an object of the present invention to prepare solid, free flowing agricultural adjuvants from nonionic surfactants of proven bioefficacy which are 100% active; contain no water-insoluble carriers; provide excellent wetting properties and serendipitously provide fertilizer activity.

It is another object of this invention to provide a dry, solid free-flowing fertilizer-surfactant powder which has low phytotoxicity, is environmentally friendly, has excellent handling properties and rapidly dissolves in water.

Other objects and advantages will be apparent from the descriptions and examples which follow.

SUMMARY OF THE INVENTION

Figure 1:
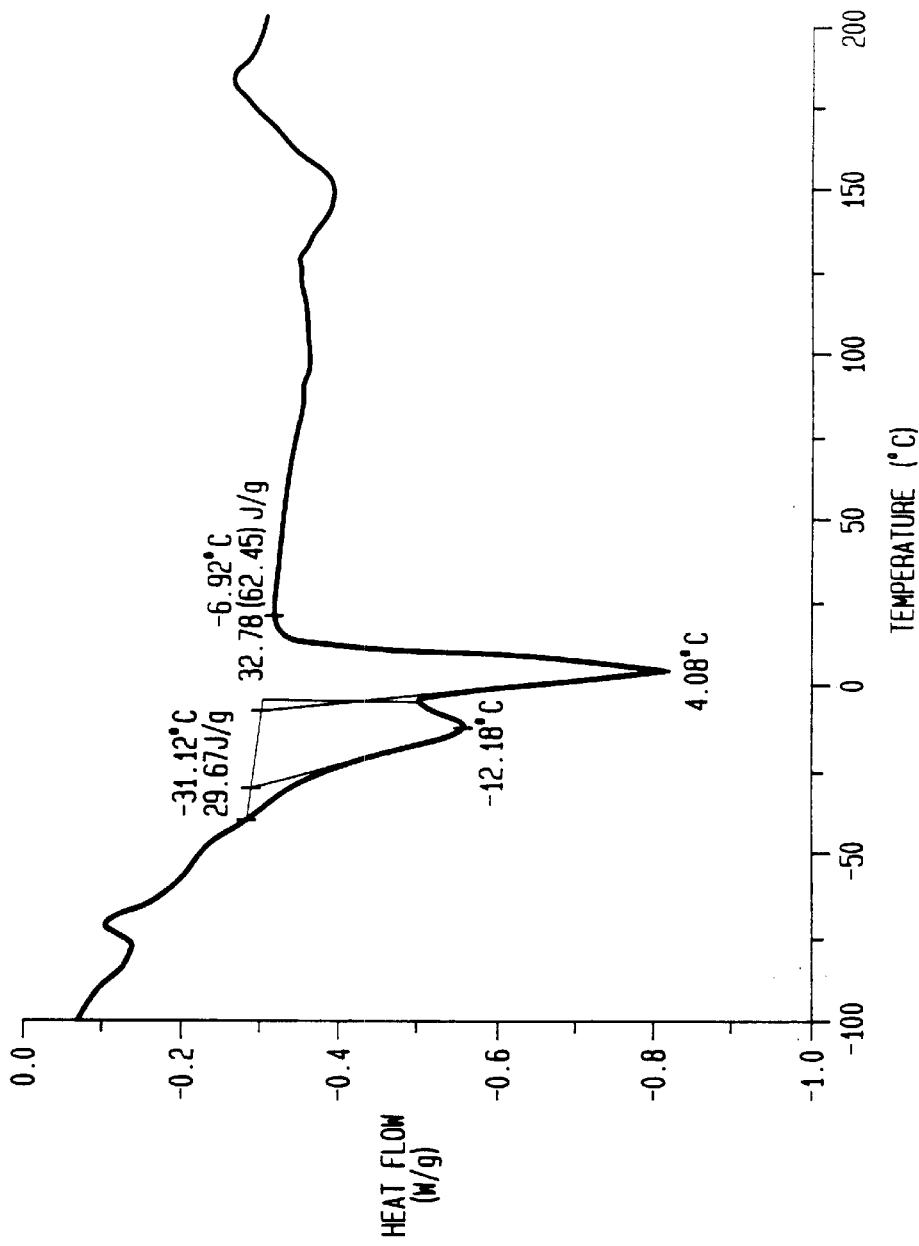
FIG. 1 is a graphic depiction of the results of a DSC scan of unclathrated SILWET L-77® polysiloxane.

The present invention relates to the discovery that certain organosilicone surfactants can be prepared as dry, solid, free-flowing complexes. The surfactants are ethoxylated polysiloxanes and, in addition to providing fertilizer characteristics, the complexes prepared therefrom are excellent adjuvants for the agricultural delivery of solid fertilizers and pesticides such as micronutrients, biologicals, insecticides, herbicides, fungicides, and plant growth regulators.

The crystalline complexes of this invention may be formed by adding the ethoxylated polysiloxane to a saturated solution of urea in water at elevated temperatures; lowering the solution temperature to crystallize the clathrate; and evaporating the water. Optionally, the material can be ground to a fine powder.

These free-flowing adducts can be included into a dry pesticide formulation to improve wetting, compatibility, buffering, or other well known adjuvancy characteristics. Alternatively, these inclusion complexes, with their rapid dissolution properties, can be added directly to the spray tank or used like any other tank-mix adjuvant. Regardless of the method used, the adjuvants of this invention will activate pesticides biologically as well as function as wetting agents, compatibility agents or fertilizer-nutrients. Enhanced activity, biologically or otherwise, achieves the desired pesticidal effect with lower levels of the more expensive pesticide active.

DETAILED DESCRIPTION OF THE INVENTION

The instant invention relates to the discovery that certain liquid organofunctional polysiloxanes, even though possessing multiple destabilizing silicon atoms; the extremely rotational and flexible Si—O—Si bonds; and very large end groups can be converted into a dry, free-flowing crystalline solid. The products of this invention are inclusion adducts or compounds of complex-forming agents with ethoxylated polysiloxanes as described below. While the exact structures of these solid complexes are not known, it is believed that at least a physical combination exists. Evidence for the existence of a complex is found in the fact that the thermal transitions for the individual components is absent (or almost entirely so) from a DSC thermogram of the product while a new thermal transition, believed to be that of the product complex, appears in the DSC thermogram. In this detailed description and the appended claims, all amounts and all numerical values for repeating units should be understood to be qualified by the term "about", unless otherwise expressly noted in context. Further, it should be noted that while the numerical values for repeating units will be whole numbers for pure compounds, the numerical values will typically be represented by number which include fractional or decimal expressions which indicate an average value for a polydisperse mixture.

The complex-forming agents are represented by the formula:

IV.

wherein X is O, S, Se, or Te; i.e., the agents are urea, thiourea, selenourea, and tellurourea respectively. The preferred complex-forming agents are urea and thiourea, with the most preferred agent being urea.

The specific liquid organofunctional polysiloxanes of this invention which have been found to unexpectedly form inclusion adducts with the complex-forming agents above are of the general formula:

V.
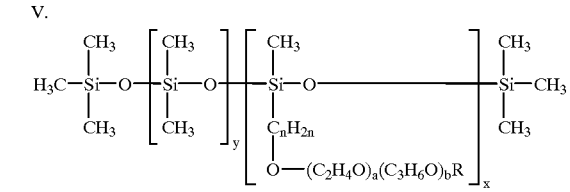

wherein n is from 2 to 6, preferably 3; a is from 6 to 25; preferably 8 to 15, and b is from 0 preferably from 0 to 15, it being understood that the oxyalkylene groups may be random and/or block mixtures of oxyalkylene units; y is in the range of from 0 to 5, preferably zero; x is in the range of from 1 to 5; preferably 1, and in which R can be hydrogen; an alkyl group having 1 to 4 carbon atoms; or an alkyl ester group wherein the alkyl group of the ester has from 1 to 4 carbon atoms.

The silicone glycols described above are known in the art and may be prepared by coupling the corresponding alkyl-terminated glycol to a bis-siloxane structure having a hydrogen attached to the central silicon atom, said structure being VI.
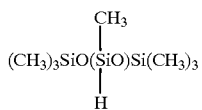

Generally, the coupling is accomplished in the presence of a platinum catalyst. In such coupling reactions, a fraction of the alkyl-terminated glycol is not converted and will remain as an impurity in the final silicone glycol product.

Silicone glycol-silicone alkane terpolymers also may be used to form the inclusions complexes of the instant invention. These compounds may be represented by the average formula:

VII. 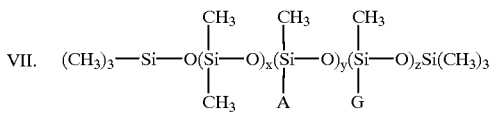

wherein A is a linear or branched alkyl radical having 6 to 30 carbon atoms, G is a glycol moiety having the formula —R' O CH$_2$CH$_2$)m OR" in which R' is a divalent alkylene group having 2 to 6 carbon atoms, R" is selected from the group consisting of hydrogen; an alkyl radical having 1 to 4 carbon atoms; an alkyl ester group wherein the alkyl group of the ester has from 1 to 4 carbon atoms; m is 8 to 100; x is 0 to 5, preferably 0; y is 0.1 to 2.5, preferably 0.1 to 1.25; 5.0, preferably 0.75 to 1.9.

The preparation of these silicone glycol-silicone alkane terpolymers which is described in U. S. Pat. No. 5,059,704 (incorporated herein) is well known in the art.

It has been found that the complexing agents identified above can form a clathrated complex with these liquid ethoxylated polysiloxanes provided that there is present an ethoxylated group at least 8 ethoxy units in length.

In order to obtain a non-tacky, i.e., dry free-flowing inclusion complex with the ethoxylated polysiloxanes of this invention, it has been observed that when the ethoxy chain length is less than about 12 units in length, the maximum weight percent of the surfactant in the complex decreases rapidly from about 50 wt. % at that chain length to about 12 weight percent when the ethoxy chains are about 8 units in length.

It is necessary that the liquid surfactants of this invention be miscible with water. Nonionic surfactants such as hydroxy ethoxylated alkylphenols have been prepared in molten urea, with or without the presence of organic solvent. However, for the preferred agricultural end uses of this invention, the melt processes are undesirable because of the possible formation of the biuret. Under melt conditions, the urea can degrade to imido-dicarbonic-diamide (a.k.a. carbamyl urea: NH$_2$ CONHCONH$_2$) a phytotoxic compound.

Although there are a variety of other methods by which complexation may be realized, e.g., freeze drying and prilling, the preferred method is as follows:
i) the water miscible ethoxylated polysiloxane is added and intimately mixed with an aqueous solution, preferably a saturated aqueous solution of a complexing agent, preferably urea at from about 50° to about 80° C.;

ii) the temperature of the polysiloxane-complexing agent solution is lowered to below the dissociation temperature of the newly formed complex; usually to below about 50° C.;
iii) the water is evaporated until a thick, non-flowing paste is formed;
iv) the paste is further dried until the water content is below about 10 weight percent by Karl Fischer titration, preferably by preparing a spread on a tray to a depth of about ¼ inch and placing the paste and tray in an oven at about 50° C.; and
v) the dried, flaked complex is ground to a fine powder.

The presence of an inclusion complex is confirmed via use of a Differential Scanning Calorimeter (DSC) (TA Instruments Model 910 DSC).

Samples are placed in a hermetic pan with a pin-hole lid and inserted into the DSC with an air flow of about 50 ml./min. The DSC is generally operated at from −50° C. to 300° C. with a temperature change rate of 10° C./min.

A number of surfactant materials containing polyethylene oxide and polypropylene oxide units have been tested, but many are either not compatible with the complexing agents of this invention or do not form solid complexes with said agents.

Whereas the exact scope of the instant invention is set forth in the appended claims, the following specific examples illustrate certain aspects of the present invention and, more particularly, point out methods of evaluating same. The examples are set forth for illustration only and are not to be construed as limitations on the present invention. All parts, ratios, and percentages are by weight unless otherwise indicated.

EXAMPLES I–IV

An aqueous solution of urea is prepared and heated to 70° C. While maintaining this temperature, a sufficient amount of an ethoxylated trisiloxane surfactant of the average formula:

VIII. 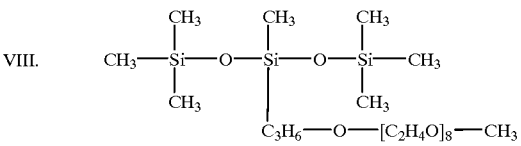

sold under the trademark SILWET L-77® by OSI Specialties, Inc. is added such that the weight ratio of surfactant to urea is 12:88. Once the surfactant and urea are in solution, the temperature is lowered to about 50° C. The solution is maintained at that temperature until sufficient water has evaporated so that a thick, non-flowing paste is formed. The paste is then spread on a tray to a depth of about ¼ inch and the tray placed in an oven at 50° C. until the water content of the inclusion complex thus formed is less than about 1 weight percent, as determined by Karl Fischer titration.

Additional samples are prepared in a like manner wherein the weight ratio of surfactant to ureais 10:90; 15:85; and 31:69.

The oven dried 10 and 12 weight percent material is subsequently ground to a fine, dry free-flowing powder. The oven dried 14 weight percent material, although able to be ground, remains very slight tacky. The oven dried 31 weight percent material remains very tacky.

DSC analysis confirms that with the 10 weight percent and 12 weight percent essentially no free polysiloxane is present and that all detectable polysiloxane has associated with the urea, by inference as inclusion complex.

Figure 2:
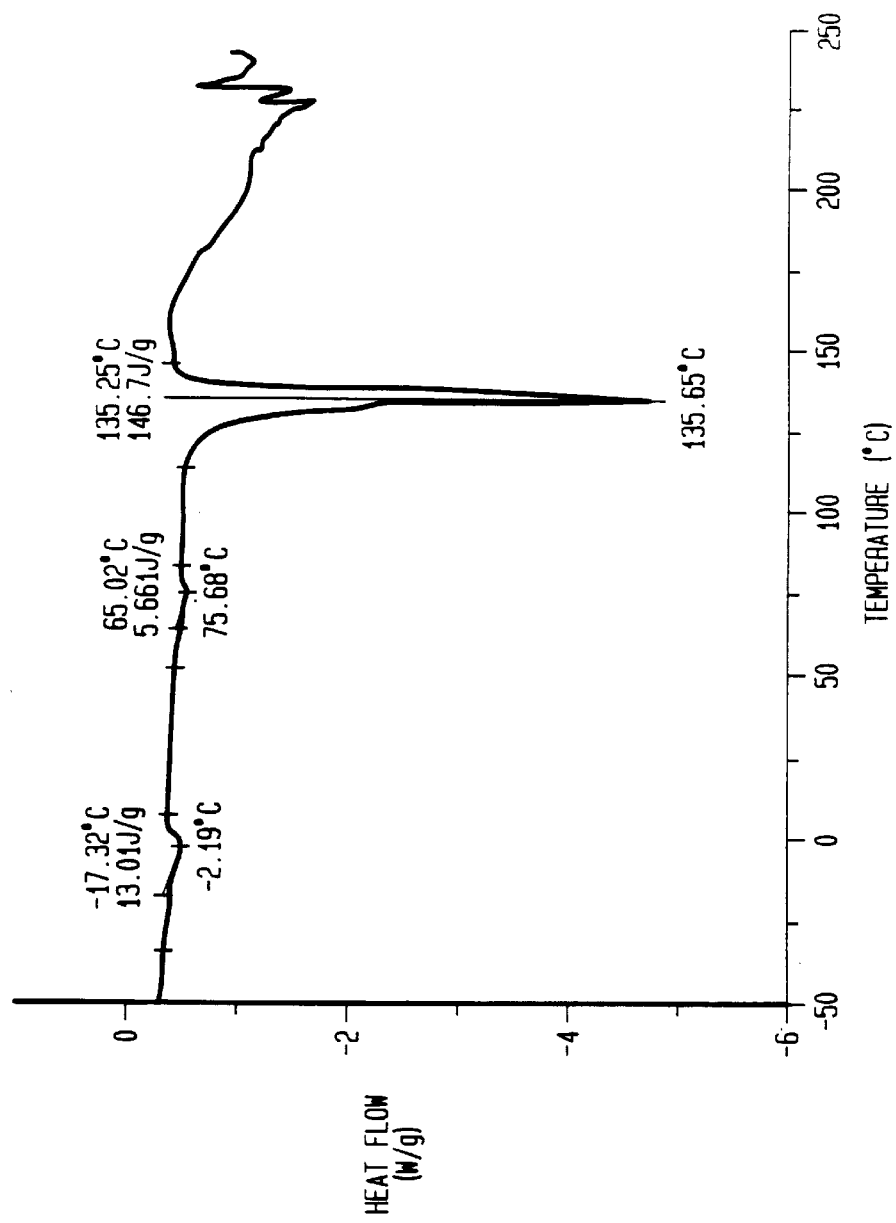
FIG. 2 is a graphic depiction of the data generated by a DSC scan of 31 weight percent of SILWET L-77® ethoxylated polysiloxane after clathration has been attempted as set forth in Example I.
Figure 3:
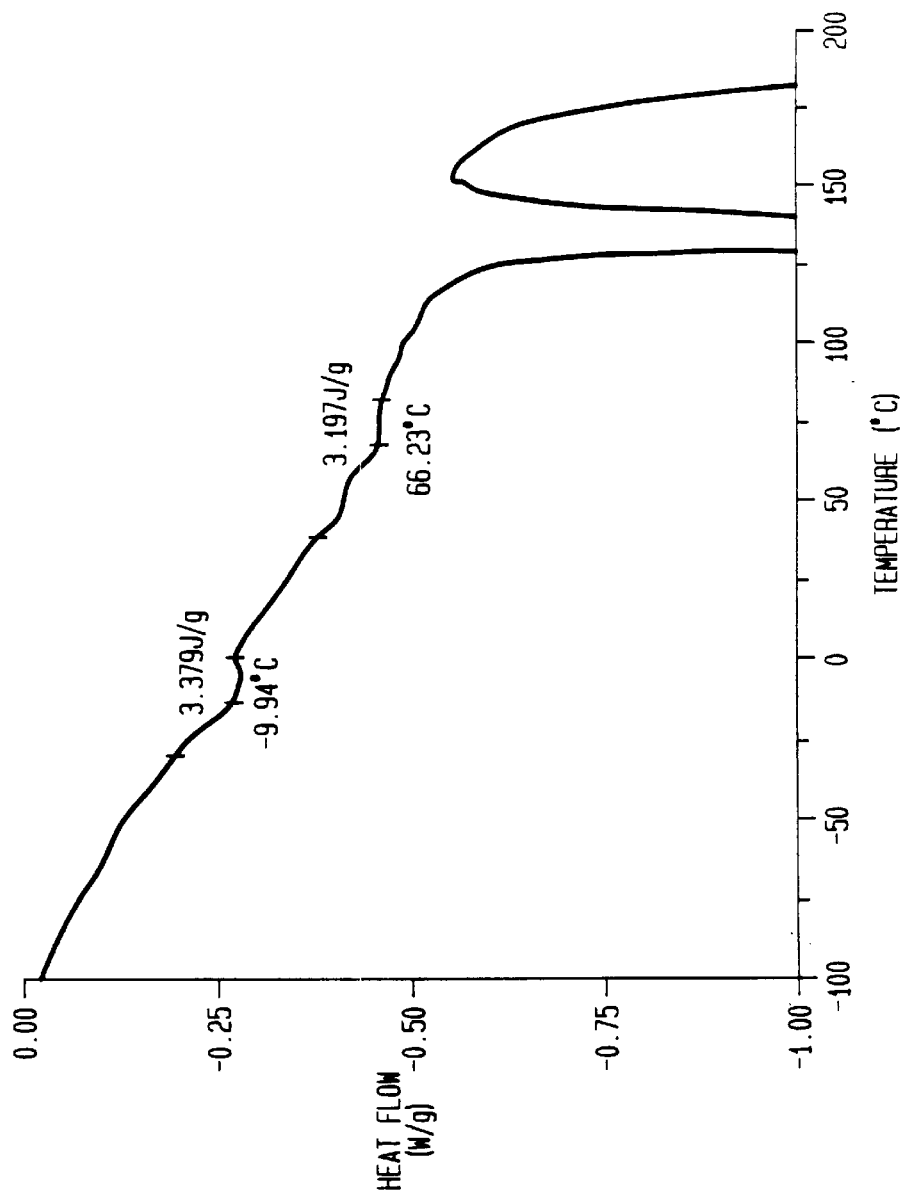
FIG. 3 is a graphic depiction of the data generated by a DSC scan of 10 weight percent SILWET L-77 ® ethoxylated polysiloxane after clathration has been attempted as set forth in Example I.

FIG. 1 is illustrative of a DSC scan of SILWET L-77 ® ethoxylated polysiloxane alone. FIG. 2 is illustrative of the DSC scanning results realized on the product obtained via the urea processing of Examples I–IV at a 31 weight percent polysiloxane loading. Note the SILWET L-77® peak at -17.320° C. FIG. 3 is a graphic depiction of the data generated by a DSC scan of 10 weight percent SILWET L-77® ethoxylated polysiloxane after clathration has been attempted as set forth in Example I.

EXAMPLE V

An aqueous solution of urea is prepared and heated to 70° C. While maintaining this temperature, a sufficient amount of the liquid ethoxylated trisiloxane surfactant of the average formula:

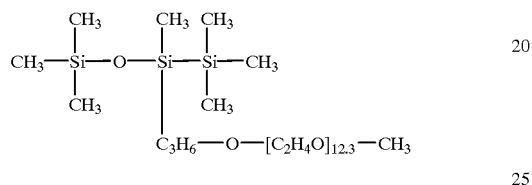

is a ed to the urea such that the weight ratio of surfactant to urea in each solution is 50:50.

Once the surfactant and urea are in solution, the temperature of the solution is lowered to about 50° C. and the procedures in Examples I–IV followed until the material has a water content below 1 weight percent.

The resulting solid forms, when ground, a fine white dry free-flowing powder. 50 grams of the dry inclusion complex powder formed from this polysiloxane was added to 1 liter of water at room temperature with moderate stirring. The complex dissolved rapidly to a clear solution.

Comparative Examples VI–X

The procedures of Examples I–IV are followed with the surfactant compounds identified in Table I below in lieu of the polysiloxane surfactant. In all cases, the weight ratio of the surfactant to urea is 10:90.

TABLE I

| A. | $CH_3$<br>$\vert$<br>$HO(CH_2CH_2O)_{13}(CH_2CHO)_{30}(CH_2CH_2O)_{13}H$ * |
| --- | --- |
| B. | $CH_3$<br>$\vert$<br>$HO(CH_2CH_2O)_{8}H(CH_2CHO)_{35}(CH_2CH_2O)_{8}$ ** |
| C. | Isotridecyl Alcohol Ethoxylate [5 EO]*** |
| D. | Isotridecyl Alcohol Ethoxylate [6 EO]*** |
| E. | Isotridecyl Alcohol Ethoxylate [7 EO]*** |

*Antarox L64; a trademark of Rhone-Poulenc Inc.
**Antarox L72; a trademark of Rhone-Poulenc Inc.
***RHODASURF Alcohol Ethoxylates; a trademark of Rhone-Poulenc Inc.

None of the above ethoxylated surfactants form a molecular inclusion complex with urea.

What is claimed is:
1. A solid, water-soluble complex comprising:
a) a water-miscible polysiloxane of the formula:

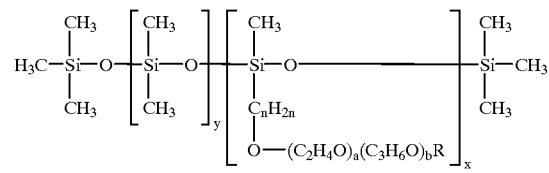

wherein n is from 2 to 6; a is from 8 to 25; and b is from 0 to 25; and the oxyalkylene groups may be random or block mixtures; y is from 0 to 5; x is from 1 to 5; and R is selected from the group consisting of hydrogen, $C_1$-$C_4$ alkyl, and a $C_1$-$C_4$, alkyl ester; or

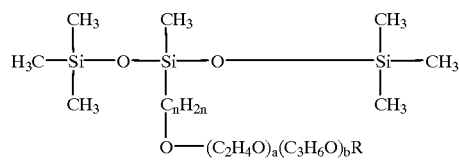

wherein A is a linear or branched alkyl having 6 to 30 carbon atoms; G is a glycol moiety of the formula —R' $(OCH_2CH_2)_m$ OR" wherein R' is a divalent alkylene group having 2 to 6 carbon atoms; R" is selected from the group consisting of hydrogen, $C_1$-$C_4$ alkyl, and a $C_1$-$C_4$ alkyl ester; m is 8 to 100; y is 0 to 5; X is 0.1 to 2.5; and z is 0.1 to 5.0; and b) a complex-forming agent of the formula:

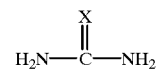

wherein X is O, S, Se, or Te.

2. The solid complex of claim 1 wherein the polysiloxane is of the formula:

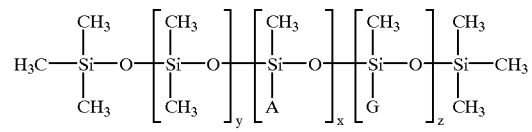

wherein n is 3; a is 8 to 15; and b is 0.

3. The solid complex of claim 2 wherein the polysiloxane is present up to 10 weight percent based on the total weight of the complex.

4. The solid complex of claim 2 wherein R is —$CH_3$ and a is 8.

5. The solid complex of claim 2 wherein the complex-forming agent is urea.

6. A solid, water-soluble complex comprising:
a) a water-miscible polysiloxane of the formula:

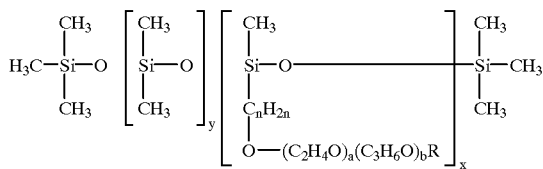

wherein n is from 2 to 6; a is from 8 to 25; and b is from 0 to 25; and the oxyalkylene groups may be random or block mixtures; y is from 0 to 5; x is from 1 to 5; and R is selected from the group consisting of hydrogen, $C_1$-$C_4$ alkyl, and a $C_1$-$C_4$, alkyl ester; and urea as a complex-forming agent.

7. The solid complex of claim 6 wherein the polysiloxane is present up to 10 weight percent based on the total weight of the complex.

8. The solid complex of claim 7 wherein y is 0, x is one, R is —$CH_3$ and a is 8.

9. An agricultural formulation comprising:
a) an agricultural chemical selected from the group consisting of pesticides and fertilizers, and
b) the complex of claim 1.

10. An agricultural formulation of claim 9 wherein said agricultural chemical is a pesticide.

11. An agricultural formulation comprising:
a) an agricultural chemical selected from the group consisting of pesticides and fertilizers, and
b) the complex of claim 2.

12. An agricultural formulation of claim 11 wherein said agricultural chemical is a pesticide.

13. An agricultural formulation comprising:
a) an agricultural chemical selected from the group consisting of pesticides and fertilizers, and
b) the complex of claim 4.

14. An agricultural formulation of claim 13 wherein said agricultural chemical is a pesticide.

15. An agricultural formulation comprising:
a) an agricultural chemical selected from the group consisting of pesticides and fertilizers, and
b) the complex of claim 6.

16. An agricultural formulation of claim 15 wherein said agricultural chemical is a pesticide.

17. An agricultural formulation comprising:
a) an agricultural chemical selected from the group consisting of pesticides and fertilizers, and
b) the complex of claim 8.

18. An agricultural formulation of claim 17 wherein said agricultural chemical is a pesticide.

19. A dry, flowable agricultural chemical concentrate comprising a blend of:
a) an agricultural chemical selected from the group consisting of pesticides and fertilizers, and
b) the complex of claim 1.

20. A concentrate of claim 19 wherein said agricultural chemical is a pesticide.

* * * * *